(12) United States Patent
Huang et al.

(10) Patent No.: US 12,355,143 B2
(45) Date of Patent: Jul. 8, 2025

(54) SIGNAL SENSING DEVICE

(71) Applicant: METAL INDUSTRIES RESEARCH & DEVELOPMENT CENTRE, Kaohsiung (TW)

(72) Inventors: Shu-Hung Huang, Kaohsiung (TW); Chun-Chieh Tseng, Kaohsiung (TW); Jui-Han Lu, Kaohsiung (TW); Chun-Ming Chen, Kaohsiung (TW); Ping-Ruey Chou, New Taipei (TW); Yen-Hsin Kuo, Kaohsiung (TW); Tung-Lin Tsai, Tainan (TW); Yen-Hao Chang, Kaohsiung (TW); Sheng-Hua Wu, Kaohsiung (TW); Chia-Hua Chang, Changhua County (TW); Wen-Ming Cheng, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 140 days.

(21) Appl. No.: 18/498,606

(22) Filed: Oct. 31, 2023

(65) Prior Publication Data
US 2025/0141091 A1 May 1, 2025

(51) Int. Cl.
*H01Q 1/27* (2006.01)
*A61B 5/00* (2006.01)
(Continued)

(52) U.S. Cl.
CPC ............ *H01Q 1/273* (2013.01); *A61B 5/026* (2013.01); *A61B 5/07* (2013.01); *A61B 5/6876* (2013.01)

(58) Field of Classification Search
CPC .......... H01Q 1/273; A61B 5/07; A61B 5/026; A61B 5/6876
See application file for complete search history.

(56) References Cited

U.S. PATENT DOCUMENTS

| 5,929,825 A | * | 7/1999 | Niu | ...................... H01Q 9/0442 |
| | | | | 343/866 |
| 8,761,896 B2 | * | 6/2014 | Vajha | ................... H01Q 9/0414 |
| | | | | 607/32 |

(Continued)

FOREIGN PATENT DOCUMENTS

| JP | 2014504903 A | 2/2014 |
| JP | 2021137138 A | 9/2021 |

(Continued)

*Primary Examiner* — Ab Salam Alkassim, Jr.
(74) *Attorney, Agent, or Firm* — WPAT, PC

(57) ABSTRACT

A signal sensing device includes a body and two signal sensing elements disposed in the body. An insulating layer is sandwiched between the two signal sensing elements. Each of the two signal sensing elements incudes a signal transmission section and a signal sensing section in electrical connection with the signal transmission section. The signal transmission sections are planar antennae parallel to each other and each having an antenna shape of meander-line type. The antenna shape of each transmission section has a vertical projection on a plane parallel to each signal transmission section. The vertical projections of the antenna shapes do not overlap completely. When a portion of the body forms a surrounding portion which surrounds a to-be-sensed target, a portion or an entirety of each signal sensing section is located on the surrounding portion.

13 Claims, 8 Drawing Sheets

(51) Int. Cl.
*A61B 5/026* (2006.01)
*A61B 5/07* (2006.01)

(56) References Cited

U.S. PATENT DOCUMENTS

| | | | |
|---|---|---|---|
| 9,125,567 B2* | 9/2015 | Gross | A61B 5/6862 |
| 9,259,585 B2 | 2/2016 | Vajha et al. | |
| 9,579,509 B2 | 2/2017 | Vajha et al. | |
| 10,004,438 B2* | 6/2018 | Huang | A61B 5/6876 |
| 10,004,908 B2 | 6/2018 | Vajha et al. | |
| 10,029,105 B2* | 7/2018 | Ameri | A61N 1/3758 |
| 10,099,059 B2 | 10/2018 | Vajha et al. | |
| 10,779,767 B2* | 9/2020 | Li | A61B 5/29 |
| 12,290,690 B2* | 5/2025 | Dubey | H01Q 1/42 |
| 2007/0013587 A1* | 1/2007 | Liu | H01Q 1/36 |
| | | | 343/702 |
| 2009/0228074 A1* | 9/2009 | Edgell | H01Q 1/40 |
| | | | 607/60 |
| 2009/0228076 A1* | 9/2009 | Ameri | H01Q 5/321 |
| | | | 607/60 |
| 2012/0126828 A1* | 5/2012 | Cohen | A61B 5/05 |
| | | | 324/629 |
| 2012/0130450 A1* | 5/2012 | Vajha | H01Q 1/36 |
| | | | 607/60 |
| 2012/0130451 A1* | 5/2012 | Vajha | H01Q 1/36 |
| | | | 607/60 |
| 2013/0041244 A1* | 2/2013 | Woias | G01L 1/142 |
| | | | 600/381 |
| 2015/0097734 A1* | 4/2015 | Zhao | H01Q 1/362 |
| | | | 29/601 |
| 2015/0255872 A1* | 9/2015 | Hasumuro | H04W 4/16 |
| | | | 455/456.1 |
| 2016/0361002 A1* | 12/2016 | Palikaras | A61B 5/1455 |
| 2018/0323090 A1* | 11/2018 | Deo | A61F 7/12 |
| 2021/0378572 A1* | 12/2021 | Beker | A61B 5/0535 |
| 2024/0138768 A1* | 5/2024 | Chun | A61B 5/6876 |
| 2024/0180492 A1* | 6/2024 | Tseng | A61B 5/026 |

FOREIGN PATENT DOCUMENTS

| | | | |
|---|---|---|---|
| JP | 7631480 B1 * | 2/2025 | |
| TW | I843669 B * | 5/2024 | |

* cited by examiner

SIGNAL SENSING DEVICE

BACKGROUND OF THE INVENTION

1. Field of the Invention

The present invention relates to a sensing technology and, more particularly, to a signal sensing device.

2. Description of the Related Art

In a conventional method of proceeding with signal measurements by surrounding a to-be-measured target for measuring physiological signals, particularly in a case that the signal sensing device cannot be directly installed in an organism by an approach without external wires, due to the interference from the measurement environment where the signal sensing device is located, the sensed signal cannot be effectively transmitted outward, such that an external analyzing device cannot obtain the associated transmission signal. As a result, the physiological state of the organism cannot be known immediately.

In light of the above, it is necessary to improve the conventional signal sensing device.

SUMMARY OF THE INVENTION

To solve the above problems, it is an objective of the present invention to provide a signal sensing device capable of enhancing the signal transmission quality.

It is another objective of the present invention to provide a signal sensing device which can be mounted inside an organism and can be degraded and absorbed by the organism as time passes.

As used herein, the term "a", "an" or "one" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

The dimensional definitions related to sizes recited herein are based on FIG. 1 of the accompanying drawings. The term "length" refers to the extending direction of the length (designated by $L_H$ or $L_E$) of the head portion or the extension portion of the body, which is the extending direction of Y axis of FIG. 1. The term "width" refers to the extending direction of the width (designated by $W_H$ or $W_E$) of the head portion or the extension portion of the body, which is the extending direction of X axis of FIG. 1. The term "thickness" (or "height") refers to the extending direction of the thickness (designated by $T_H$ or $T_E$) of the head portion or the extension portion of the body, which is the extending direction of Z axis of FIG. 1. Furthermore, the size referred to herein may be adjusted by 0.1 µm per adjustment. Furthermore, the "working frequency" referred to herein may be adjusted by 1 MHz per adjustment. Furthermore, the numerical value mentioned herein may have a tolerance of ±10%.

A signal sensing device according to the present invention includes a body and two signal sensing elements disposed in the body. An insulating layer is sandwiched between the two signal sensing elements. Each of the two signal sensing elements incudes a signal transmission section and a signal sensing section in electrical connection with the signal transmission section. The signal transmission sections are planar antennae parallel to each other and each having an antenna shape of meander-line type. The antenna shape of each transmission section has a vertical projection on a plane parallel to each signal transmission section. The vertical projections of the antenna shapes do not overlap completely. When a portion of the body forms a surrounding portion which surrounds a to-be-sensed target, a portion or an entirety of each signal sensing section is located on the surrounding portion.

Therefore, by the arrangement of the antenna shapes of meander-line type of the signal transmission sections of the signal transmission elements according to the present invention and the non-entire overlapping (misalignment) arrangement, the signal transmission effect can be enhanced effectively.

In an example, each antenna shape has a winding section line width of 0.05-0.55 mm, a winding section spacing of 1-4 mm, a winding section overall width of 5-20 mm, a winding section overall length of 5-20 mm, and a thickness of 0.005-0.1 mm. Preferably, the winding section line width is 0.15-0.2 mm, the winding section spacing is 2-3 mm, the winding section overall width is 14-16 mm, the winding section overall length is 14-16 mm, and the thickness is 0.01-0.015 mm. Therefore, by the disposition of the size of the antenna shapes of the signal transmission sections, when the signal sensing device is mounted in the to-be-sensed target to proceed with signal sensing, the strength of signal transmission can be enhanced significantly.

In an example, the vertical projections of the antenna shapes do not overlap completely and have a misalignment spacing of 0.05-2 mm. Preferably, the misalignment spacing is 0.1-1.5 mm. More preferably, the misalignment spacing is 0.5-1.5 mm. Optionally, the vertical projections of the antenna shapes do not overlap completely and each have an X-direction misalignment spacing in an X direction and a Y-direction misalignment spacing in a Y direction perpendicular to the X direction. Each of the X-direction misalignment spacing and the Y-direction misalignment spacing is 0.05-2 mm. Therefore, by the disposition of the misalignment spacing, the strength of signal transmission can be enhanced significantly.

In an example, the body includes a head portion and an extension portion connected to the head portion. The extension portion extends outward from an end of the head portion and has a length to surround the to-be-sensed target by an entirety or a portion of the extension portion. Therefore, by the disposition of the head portion and the extension portion, the signal sensing device is suitable for disposition surrounding a to-be-sensed target.

In an example, each signal transmission section is disposed on the head portion of the body, and each signal sensing section is disposed on the extension portion of the body. Therefore, by the disposition of the signal transmission section and the signal sensing section respectively corresponding to the head portion and the extension portion, the structures of the signal sensing device for the transmission function and the sensing function are properly disposed to avoid mutual interference between the transmission signal and the sensing signal.

In an example, the head portion of the body has a length and a width both of which are 5-35 mm. The extension portion has a width of 2-15 mm. Each of the head portion and the extension portion has a thickness of 0.05-0.350 mm. Therefore, by the disposition of the above sizes, the signal sensing device may be suitable for a specific environment having a limited space (such as the anterior of a human, a rabbit, or a mouse, or the interior of a larger organism) and for sensing signals associated with a specific to-be-sensed target (such as an organ or a tissue).

In an example, the signal sensing device further includes a signal amplifying portion having a plurality of protruding structures protruding outward from the body. Each of the plurality of protruding structures is cylindrical and has a diameter of 250-400 μm (preferably 300-350 μm) and a height of 40-75 μm (preferably 50 μm). When the surrounding portion is formed by a portion of the body, the signal amplifying portion is partially or entirely in contact with the to-be-sensed target. Therefore, by the disposition of the above specific shape and size of the protruding structures, when the signal sensing device is disposed around the to-be-sensed target to proceed with signal sensing, the strength of the sensing signal can be enhanced significantly.

In an example, the signal sensing device is made of one or more bio-degradable materials.

Therefore, by the provision of the biodegradable signal sensing elements according to the present invention, the signal sensing device made of biodegradable material is suitable for installation in an organism to sense the interested signals and can degrade completely in a predetermined period of time without the need of removal by operation, thereby avoiding the risk caused by the second operation.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
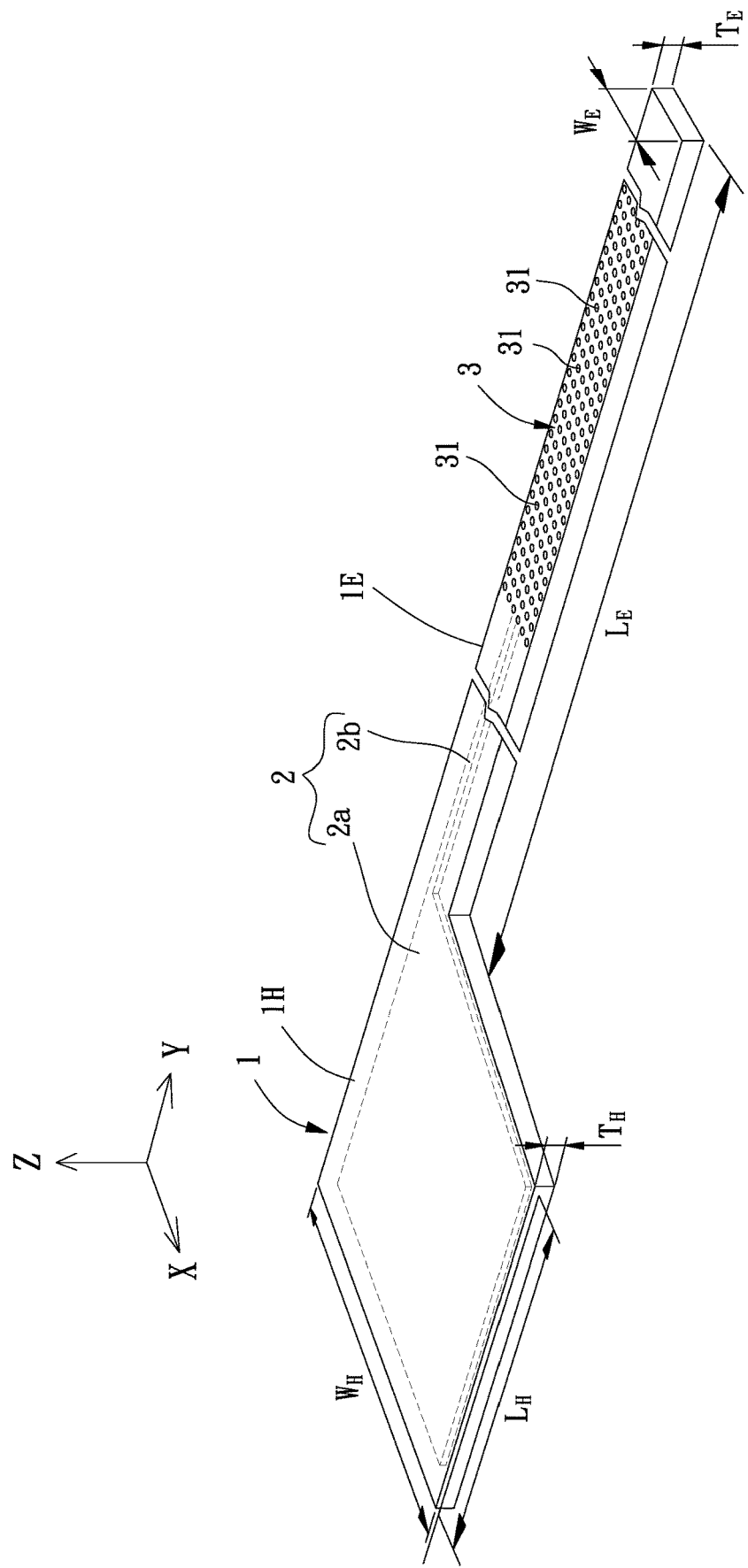
FIG. 1 is a diagrammatic perspective view of a signal sensing device of a preferred embodiment according to the present invention.

When the terms "front", "rear", "left", "right", "up", "down", "top", "bottom", "inner", "outer", "side", and similar terms are used herein, it should be understood that these terms have reference only to the structure shown in the drawings as it would appear to a person viewing the drawings and are utilized only to facilitate describing the invention, rather than restricting the invention.

DETAILED DESCRIPTION OF THE INVENTION

Figure 2:
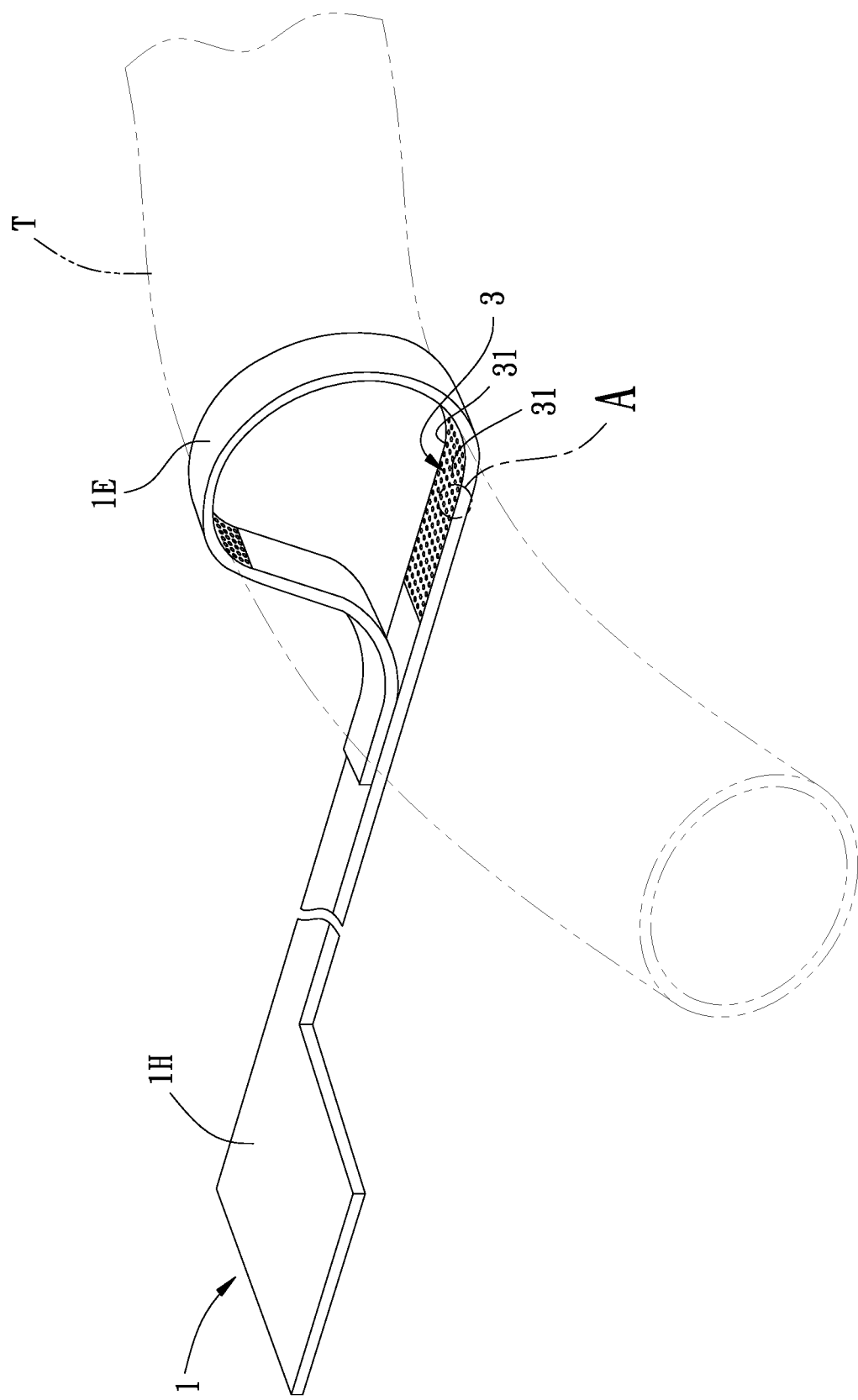
FIG. 2 is a diagrammatic view illustrating disposition of the signal sensing device of FIG. 1 around a to-be-sensed target.

FIGS. 1 and 2 show an example of a signal sensing device of a preferred embodiment according to the present invention and a to-be-sensed target surrounded by the signal sensing device. The signal sensing device includes a body 1 and a signal sensing element 2. A portion of the body 1 forms a surrounding portion configured to surround a to-be-sensed target T. The signal sensing element 2 is mounted in the body 1. Preferably, the to-be-sensed target T is an organ or a tissue of an organism. It is noted that the to-be-sensed target T shown in FIG. 2 is a blood vessel. Nevertheless, the to-be-sensed target T is not limited in this regard.

Optionally, the signal sensing device may further include a signal amplifying portion 3 disposed on the body 1. When a portion of the body 1 surrounds the to-be-sensed target T, the signal amplifying portion 3 is partially or entirely in contact with the to-be-sensed target T.

The body 1 is used to envelop the signal sensing element 2 to protect the signal sensing element 2 and to reduce the interference from the sensing environment to the signal sensing element 2. Optionally, the body 1 is in the form of a long strip and preferably has a wider area to surround the to-be-sensed target T. Optionally, the body 1 is a long strip and has a uniform size, such as in the length, width, and thickness. Optionally, as shown in FIGS. 1 and 2, the body 1 is a long strip and includes a head portion 1H and an extension portion 1E connected to the head portion 1H. The extension portion 1E extends outward from an end of the head portion 1H and has a length to surround the to-be-sensed target T by an entirety or a portion of the extension portion 1E. Particularly, a portion of the extension portion 1E forms an annular object to surround the to-be-sensed target T. When the extension portion 1E forms the annular object, a free end of the extension portion 1E or a portion near the free end may be fixed to a proper portion of the extension portion 1E per se, such that the body 1 may securely surround the to-be-sensed target T. The method for fixing the extension portion 1E may be selected according to the actual situation. The present invention is not limited in this regard.

With regard to the disposition of the size of the body 1, particularly in the case that the signal sensing device is mounted in a human body to measure a blood vessel, with reference to the axes X, Y, and Z shown in FIG. 1, the head portion 1H of the body 1 has a length $L_H$ (corresponding to the extending direction of Y axis) and a width $W_H$ (corresponding to the extending direction of X axis). Both the length $L_H$ and the width $W_H$ are 5-35 mm, preferably 10-30 mm, and more preferably 15-20 mm. The head portion 1H further has a thickness $T_H$ (corresponding to the extending direction of Z axis) of 0.05-0.35 mm. The extension portion 1E has a width $W_E$ of 2-15 mm, preferably 5-10 mm, and a thickness $T_E$ of 0.05-0.35 mm. Furthermore, the length $L_E$ of the extension portion 1E is disposed according to the actual need.

As shown in FIG. 1, the number of the signal sensing element 2 is at least one. Each signal sensing element 2 incudes a signal transmission section 2a and a signal sensing section 2b in electrical connection with the signal transmission section 2a and is disposed in the body 1. In a case that a portion of the body 1 forms a surrounding portion which surrounds the to-be-sensed target T, a portion or an entirety of the signal transmission section 2a is located on the surrounding portion. Specifically, the signal transmission section 2a is located on the head portion 1H of the body 1 and may have an antenna structure to convert a sensing signal generated by the signal sensing section 2b (particularly a sensing signal generated in association with the to-be-sensed target T) into a transmission signal (such as an electromagnetic wave) having a specific working frequency. The transmission signal is sent out, particularly to a signal analysis device (not shown), and the transmission signal is converted into information to be monitored, permitting associated analysis or monitoring management. The signal sensing section 2b is located on the extension portion 1E of the body 1 and is distributed in an area of the body 1 which surrounds the to-be-sensed target T. The signal sensing section 2b receives to-be-monitored information (such as the blood flow rate) of the to-be-sensed target T (such as a blood vessel) and converts the to-be-monitored information into a sensing signal (such as an electric signal). Then, the signal sensing section 2b transmits the sensing signal to the signal transmission section 2a which generates an associated transmission signal. Specifically, the transmission signal may be transmitted to a corresponding receiving unit (not shown) which may analyze the received transmission signal according to a predetermined approach and which may convert the transmission signal into the to-be-monitored information of the to-be-sensed target T, thereby observing, analyzing, or monitoring the change of the to-be-monitored information.

Specifically, the antenna structure is a flat antenna or planar antenna. The working frequency may be decided according to the antenna pattern of the signal transmission section 2a. Namely, given the same material and size, different working frequencies may be obtained via different antenna patterns. The antenna pattern may be comprised of at least one of a square loop, a circular loop, a triangular loop, a non-symmetric loop, and other patterns. According to research of the present invention, when the signal sensing device according to the present invention is mounted in a human body, a better transmission effect may be obtained when the working frequency is 350-450 MHz. Preferably, the working frequency is 401-406 MHz. Thus, in the above working frequency range, the signal transmission section 2a may proceed with signal transmission with a stable signal quality.

Figure 3:
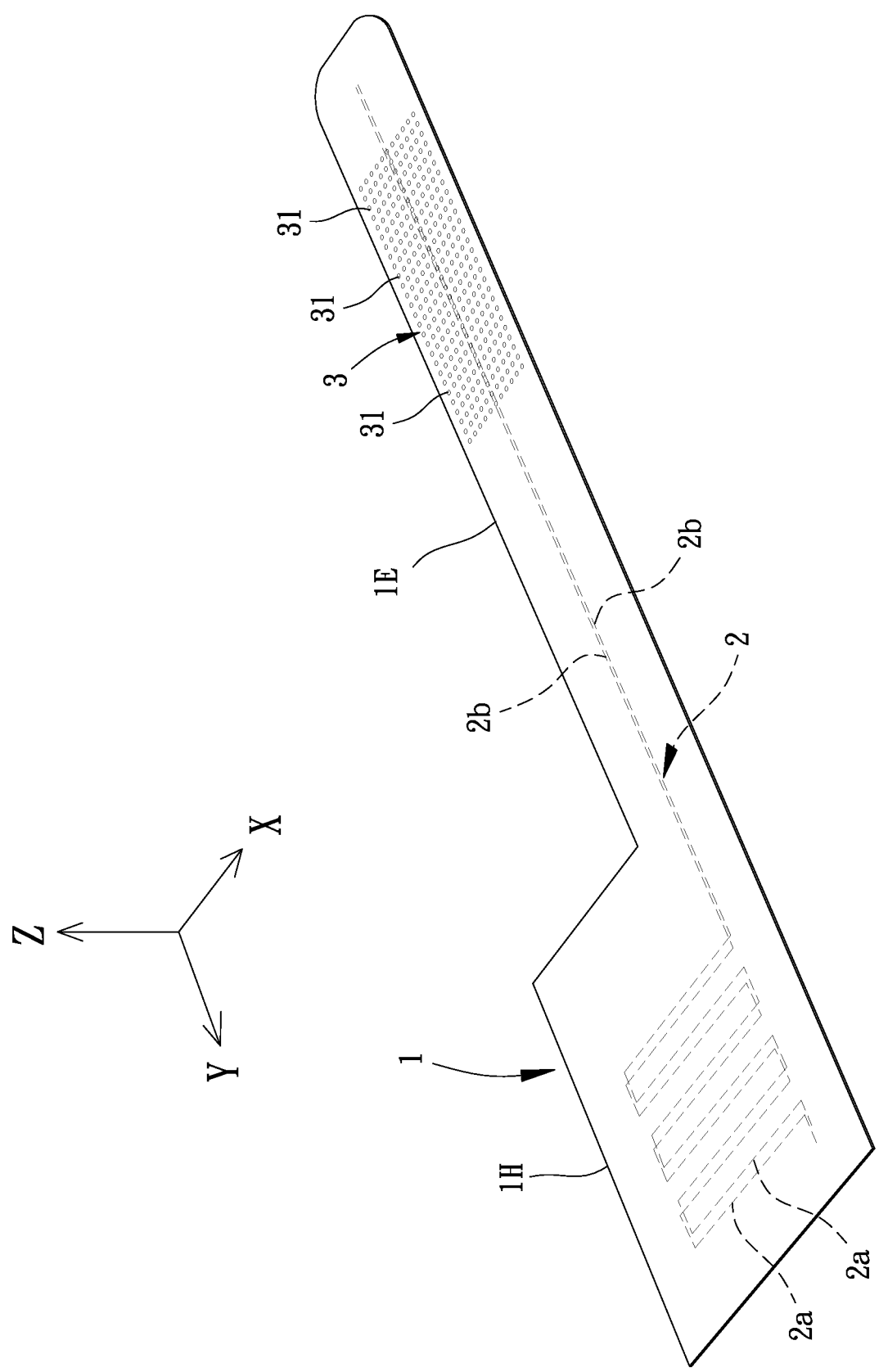
FIG. 3 is a diagrammatic perspective view illustrating a preferred embodiment of signal sensing elements according to the present invention.

Optionally, as shown in FIG. 3, the signal sensing device may have a plurality of signal sensing elements 2, and an insulating layer I may be disposed between each two adjacent signal sensing elements 2. The insulating layer I separates the signal sensing elements 2 and avoids mutual signal interference of the signal sensing elements 2. Preferably, the number of the signal sensing elements 2 is two, and an insulating layer I is sandwiched between the two signal sensing elements 2. In association with the length (with reference to Y axis), width (with reference to X axis), and thickness/height (with reference to Z axis) of the body 1, the thickness of each of the signal transmission section 2a and the signal sensing section 2b is 0.005-0.1 mm. Regarding the size disposition of the length and width of the signal transmission section 2a and the signal sensing section 2b, the signal transmission section 2a and the signal sensing section 2b are respectively disposed in association with the head portion 1H and the extension portion 1E of the body 1. Particularly, the lengths and widths of the signal transmission section 2a and the signal sensing section 2b are smaller than those of the head portion 1H and the extension portion 1E, such that the signal sensing elements 2 can be mounted in the body 1.

Figure 4:
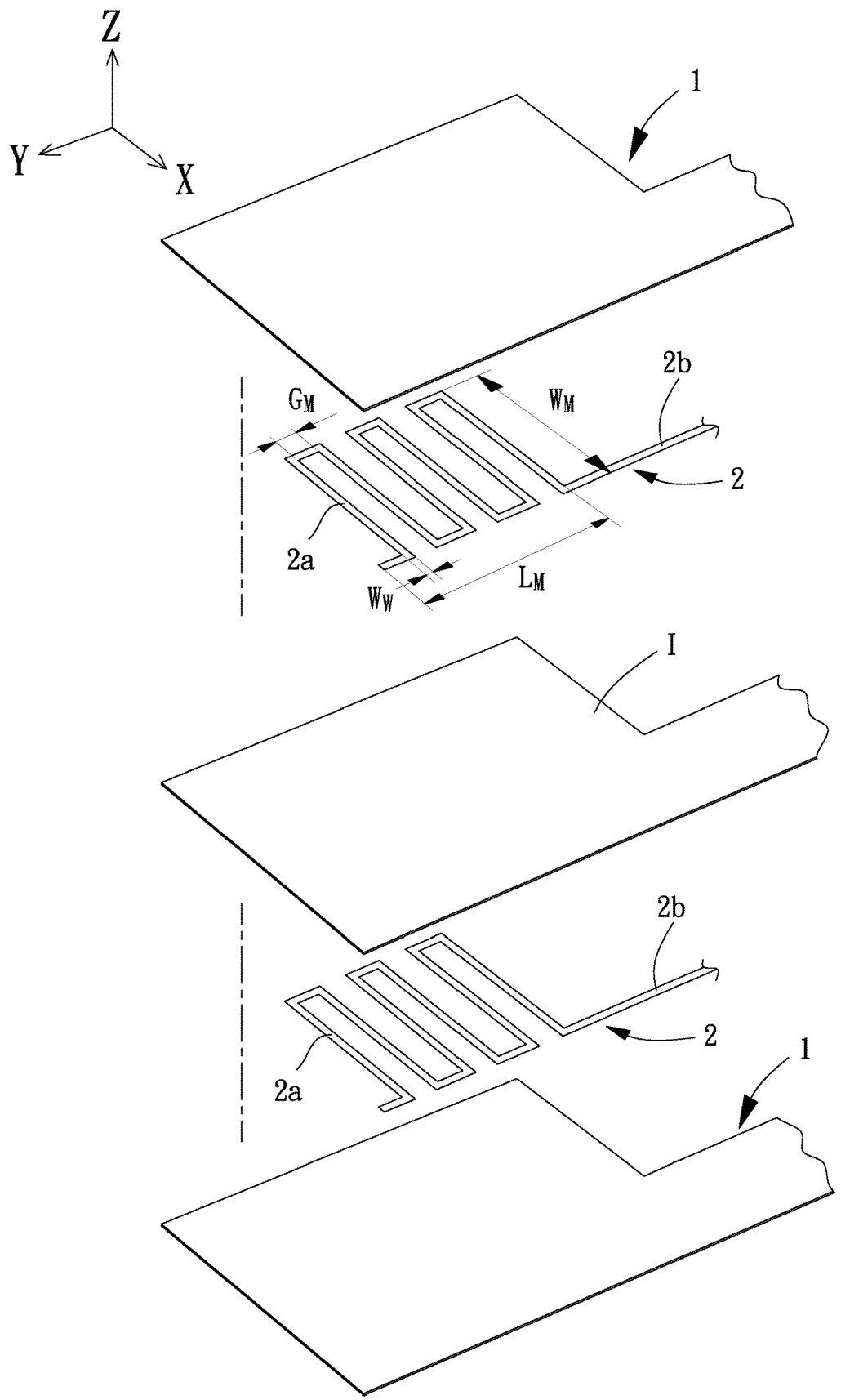
FIG. 4 is a diagrammatic partial, exploded, perspective view of the signal sensing elements of FIG. 3.
Figure 5:
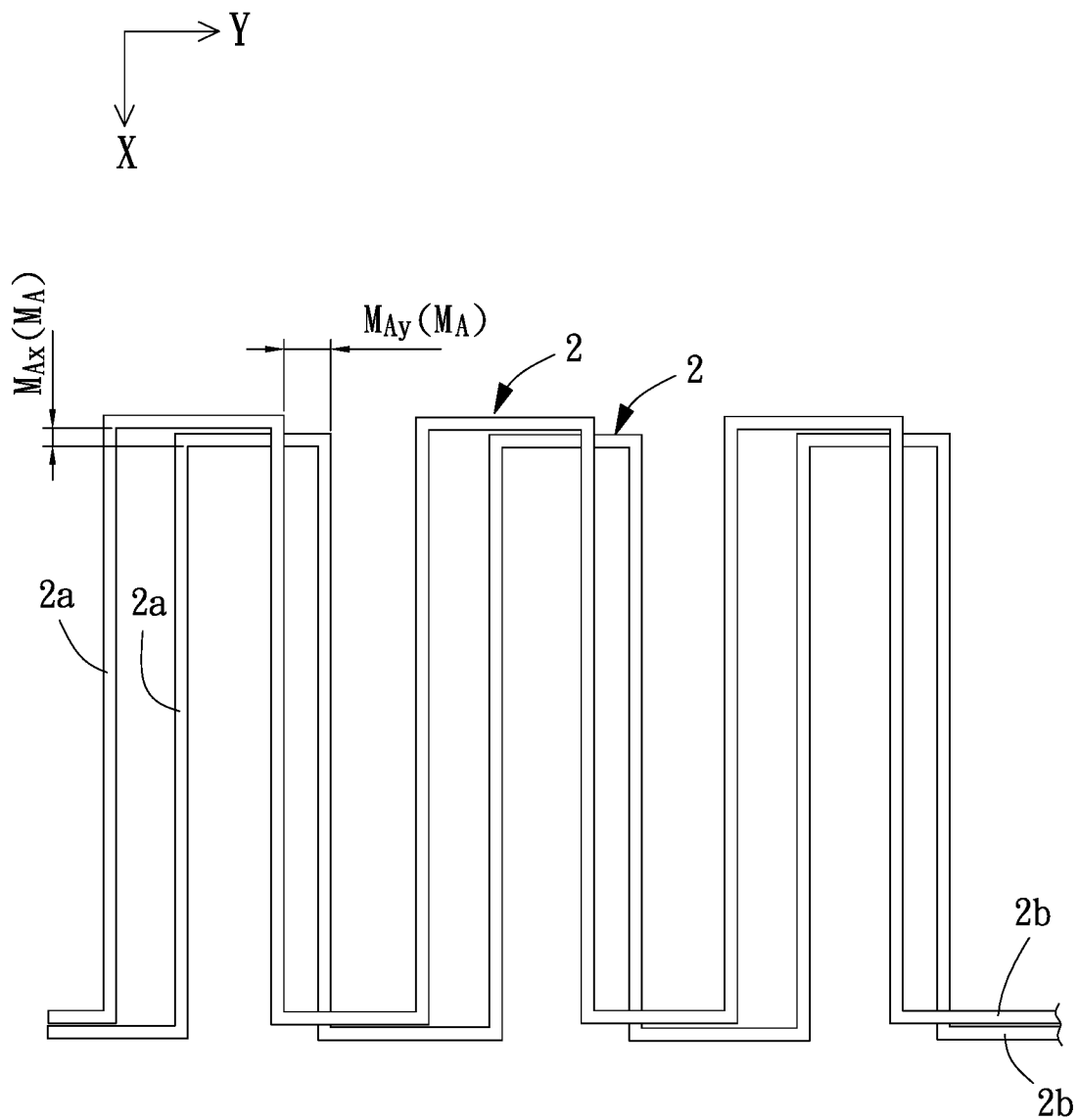
FIG. 5 is a diagrammatic top view illustrating misalignment of the signal transmission sections of FIG. 4.

Particularly, as shown in FIGS. 3-5, according to research of the present invention, the number of the signal sensing elements 2 is two. The signal transmission sections 2a of the signal sensing elements 2 are planar antennae parallel to each other and each having an antenna shape of meander-line type. The signal sensing elements 2 overlap with each other (with reference to the Z axis) and have an insulating layer I sandwiched therebetween, and the antenna shapes are misaligned. Particularly, the antenna shape of each transmission section 2a has a vertical projection on a plane (the X-Y plane) parallel to each signal transmission section 2a. The vertical projections of the antenna shapes do not overlap completely. Therefore, the signal sensing device is suitable for use in the human body to convert the obtained sensing signal into a high-quality transmission signal. Specifically, as shown in FIG. 4, each antenna shape of meander-line type has a winding section line width $W_W$ of 0.05-0.55 mm (preferably 0.09-0.25 mm, and more preferably 0.15-0.2 mm), a winding section spacing $G_M$ of 1-4 mm (preferably 2-3 mm), a winding section overall width $W_M$ of 5-20 mm (preferably 14-16 mm), a winding section overall length LM of 5-20 mm (preferably 14-16 mm), and a thickness of 0.005-0.1 mm (preferably 0.01-0.05 mm, and more preferably 0.01-0.015 mm). It is noted that the size (in each direction) of the winding section of each antenna is smaller than that of the corresponding portion of the body 1, particularly the head portion 1H. Preferably, as shown in FIG. 5, the vertical projections of the antenna shapes do not overlap completely and have a misalignment spacing $M_A$ of 0.05-2 mm, preferably 0.1-1.5 mm, and more preferably 0.5-1.5 mm. Optionally, the misalignment spacing $M_A$ includes an X-direction misalignment spacing $M_{Ax}$ along the X axis and a Y-direction misalignment spacing $M_{Ay}$ along the Y axis. The misalignment spacing $M_A$ is defined as the length comprised of the X-direction misalignment spacing $M_{Ax}$ and the Y-direction misalignment spacing $M_{Ay}$ ($M_A^2 = M_{Ax}^2 + M_{Ay}^2$). Each of the X-direction misalignment spacing $M_{Ax}$ and the Y-direction misalignment spacing $M_{Ay}$ is 0.05-2 mm, preferably 0.1-1.5 mm, and more preferably 0.5-1.5 mm).

Figure 6:
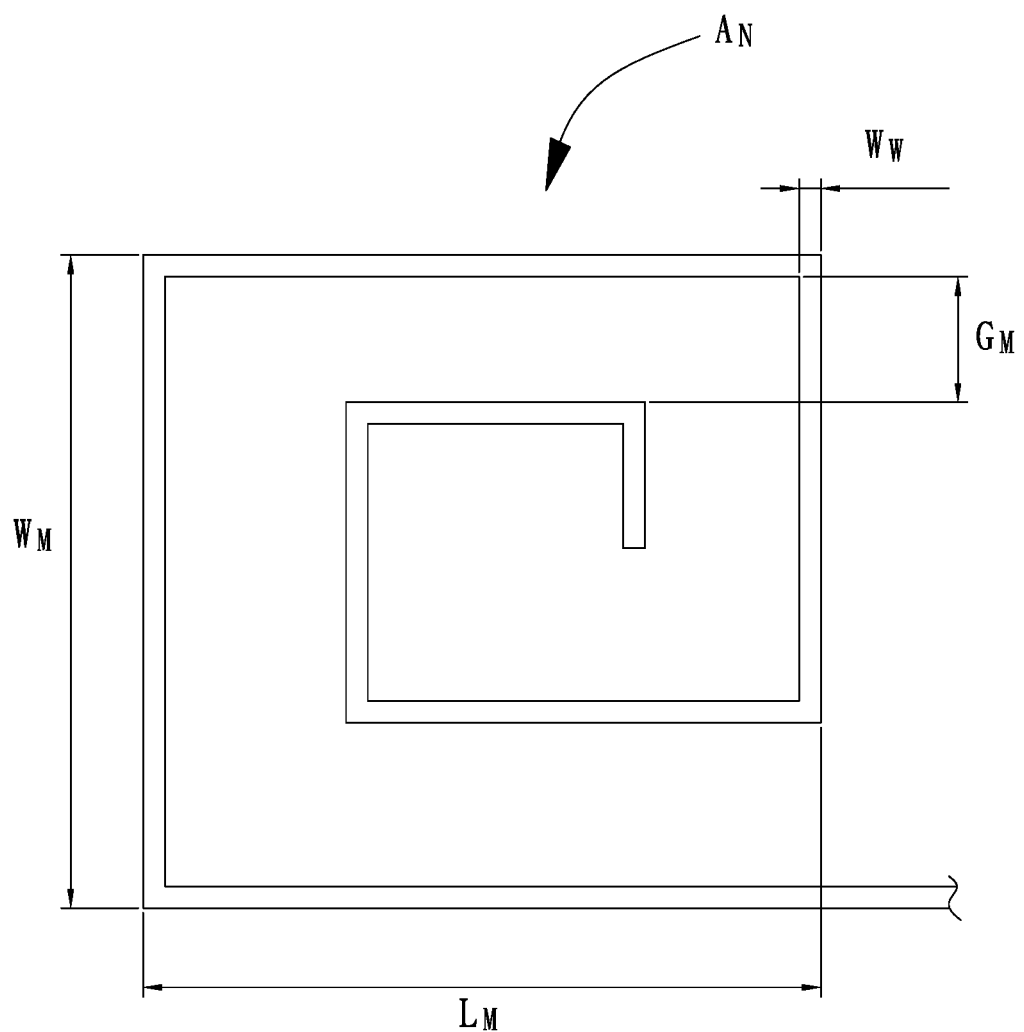
FIG. 6 is a diagrammatic top view illustrating a spiral antenna used in a comparison experiment.

Please refer to Table 1 below showing the return loss and the antenna efficiency obtained from different antenna dispositions and sizes. Dispositions 1-3 in Table 1 are the antenna data which is designed for a human body blood signal sensing device and published by Stanford University Research Team. Particularly, the antenna of the signal sensing device is a spiral antenna which is in the form of a square loop shown in FIG. 6 (only one antenna AN is diagrammatically illustrated). The data which is unable to be acquired or estimated is represented by "no data". Dispositions 4-7 in Table 1 are the research data of the present invention.

TABLE 1

| | | Return loss and antenna efficiency of each antenna disposition | | | | | |
|---|---|---|---|---|---|---|---|
| Disposition | Shape | Upper antenna line width $W_W$ | Lower antenna line width $W_W$ | Spacing $G_M$ | Misalignment $M_A$ | Return Loss | Antenna efficiency at 400 MHz |
| 1 | Spiral | 1.5 mm | 1.5 mm | No data | 0.5 mm | Central frequency 700 MHz | No data |

TABLE 1-continued

Return loss and antenna efficiency of each antenna disposition

| Disposition | Shape | Upper antenna line width $W_W$ | Lower antenna line width $W_W$ | Spacing $G_M$ | Misalignment $M_A$ | Return Loss | Antenna efficiency at 400 MHz |
|---|---|---|---|---|---|---|---|
| 2 | Spiral | 0.5525 mm | 0.5525 mm | 0.3 mm | 0.9 mm | Bandwidth 100 MHz Central frequency 545 MHz | <0.001% |
| 3 | Spiral | 0.2025 mm | 0.3025 mm | 0.3 mm | 0.9 mm | Bandwidth 210 MHz Central frequency 545 MHz | <0.001% |
| 4 | Meander-line | 0.1 mm | 0.09 mm | 2.25 mm | 0.7 mm | Bandwidth 145 MHz Central frequency 442 MHz | About 0.030% |
| 5 | Meander-line | 0.2 mm | 0.15 mm | 2.25 mm | 0.7 mm | Bandwidth 70 MHz Central frequency 485 MHz | About 0.055% |
| 6 | Meander-line | 0.05 mm | 0.05 mm | 1 mm | 0.45 mm | Bandwidth 150 MHz Central frequency 420 MHz | <0.001% |
| 7 | Meander-line | 0.058 mm | 0.008 mm | 1 mm | 0.45 mm | Bandwidth 70 MHz Central frequency 510 MHz Bandwidth 165 MHz | <0.001% |

The bandwidth of return loss is calculated by the portion exceeding −10 dB.

As can be seen from Table 1, disposition 4 of the present invention has the best effect. Disposition 4 is based on the disposition of the transmission section 2a having the meander-line antenna. Particularly, the winding section line width $W_W$ is 0.15-0.2 mm, the winding section spacing $G_M$ is 2-3 mm, the winding section overall width $W_M$ is 14-16 mm, the winding section overall length $L_A$ is 14-16 mm, the thickness is 0.01-0.015 mm, and the misalignment spacing $M_A$ is 0.5-1.5 mm.

It is noted that the preferred working frequency (401-406 MHz) referred to herein the present invention is defined by the present transmission regulations of the medical communication devices. Furthermore, with regard to the antenna efficiency, in practical applications, the device according to the present invention is mounted in a position several centimeters under the skin, or even smaller than 1 centimeter. Furthermore, according to the research of the present invention, when the antenna efficiency is about higher than 0.010%, the transmitted signal strength may ensure the overall signal stability, such that the receiving device external to the human body can receive the corresponding transmission signal.

Figure 7:
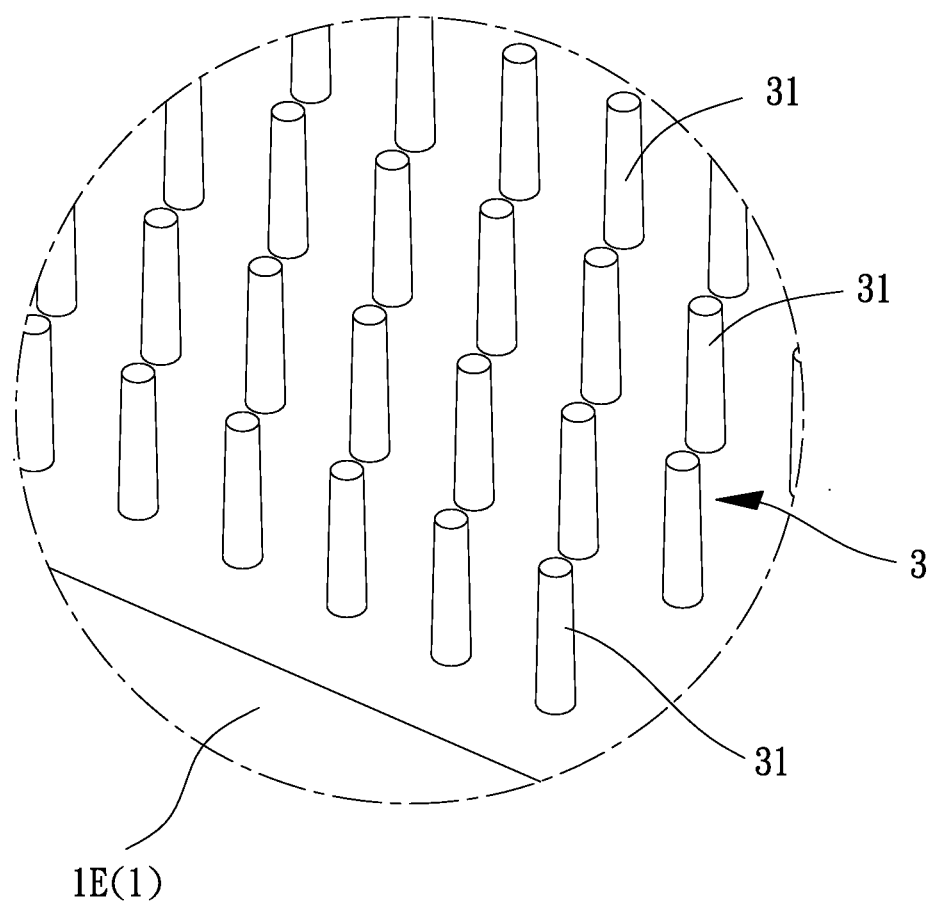
FIG. 7 is an enlarged view of a portion of a signal amplifying portion of FIG. 1.

In an embodiment of the signal sensing device having the signal amplifying portion 3, as shown in FIGS. 1, 2, and 7, the signal amplifying portion 3 has a plurality of protruding structures 31 protruding outward from an outer side of the body 1 to form a plurality of protrusive shapes. In a case that a portion of the body 1 forms a surrounding portion which surrounds the to-be-sensed target T, a portion or an entirety of the signal amplifying portion 3 is located on the surrounding portion, and the signal amplifying portion 3 is partially or entirely in contact with the to-be-sensed target T. Specifically, when the signal sensing device according to the present invention is in an extended state placed on a plane, as shown in FIG. 1, the plurality of protruding structures 3 protrudes in a direction away from the body 1. Particularly, the signal amplifying portion 3 protrudes from the extension portion 1E of the body 1 and is aligned with the signal sensing section 2b of the signal sensing element 2, such that when the body 1 surrounds the to-be-sensed target T, a portion or all of the plurality of protruding structures 31 of the signal amplifying portion 3 are in contact with the to-be-sensed target T, such that the signal amplifying portion 3 can contact with the to-be-sensed target T more closely, thereby enhancing the strength of the sensing signal (associated with the to-be-monitored information) received by the signal sensing section 2b. Optionally, each of the plurality of protruding structures 31 may be cylindrical, semi-circular, semi-elliptic, or trapezoidal in cross section. However, the shapes of the cross sections of the protruding structures 31 are not limited in this regard.

Preferably, when the plurality of protruding structures 31 is in contact with the to-be-sensed target T, the plurality of protruding structures 31 is partially or entirely pressed in the to-be-sensed target T. Particularly, the press in refers to a situation that the to-be-sensed target T is softer than the plurality of protruding structures 31, and in response to the body 1 (surrounding the to-be-sensed target T) turning from loose into tight, each of the plurality of protruding structures 31 in contact with the to-be-sensed target T will make the depressions in the contacted area of the to-be-sensed target T turn from shallow into deep. It is noted that the press in preferably does not adversely affect the normal function of the to-be-sensed target T and does not damage the to-be-sensed target T. Therefore, by partially or entirely pressing plurality of protruding structures 31 in the to-be-sensed target T, the contact area between the signal amplifying portion 3 and the to-be-sensed target T can be increased, thereby enhancing the strength of the sensing signal (associated with the to-be-monitored information) received by the signal sensing section 2b.

The length, width, and height of each of the plurality of protruding structures 31 is 0.1-500 μm. Particularly, according to the research of the present invention, the sensed signal is significantly enhanced when the plurality of protruding structures 31 is cylindrical. Specifically, in the disposition of the cylindrical protruding structures 31, each of the plurality of protruding structures 31 has a diameter of 10-500 μm (preferably 250-400 μm, and more preferably 300-350 μm) and a height of 1.5-100 μm (preferably 40-75 μm, and more preferably 50 μm). Each two protruding structures 31 have a spacing between the centers thereof, and the spacing is 1.5-5 times the diameter, preferably 2-3.5 times the diameter.

Figure 8:
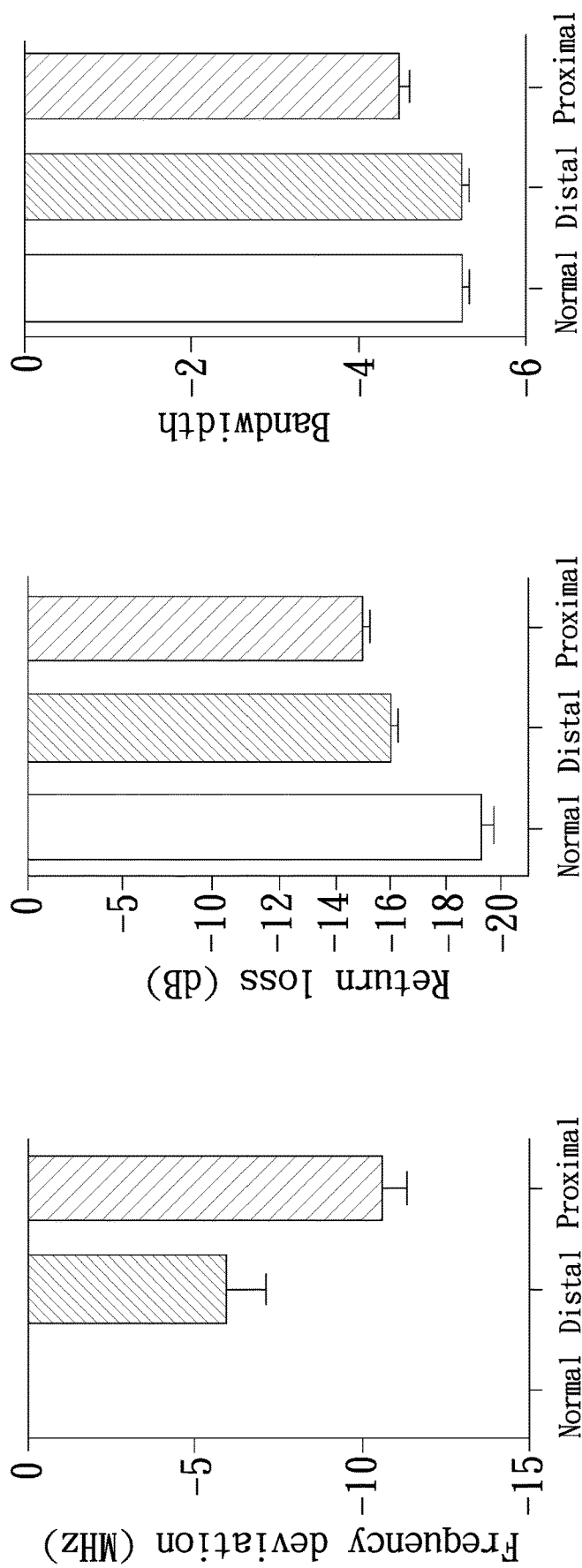
FIG. 8 is a diagrammatic view illustrating signal characteristics of a vein sensed by the signal sensing device according to the present invention.

It is noted that based on the shape and size of the protruding structures 31 according to the present invention, when the signal sensing device according to the present invention is used to measure the blood signal of an artery or a vein, particularly used to measure the vein signal, no matter the blood vessel is during the period of vasoconstriction or relaxation, a trend of change in the blood flow rate can still be obtained stably. Specifically, FIG. 8 illustrates the signal characteristics of a vein (the to-be-sensed target T) of an organism, with the vein surrounded and measured by the signal sensing device having the plurality of protruding structures 31 according to the present invention. Furthermore, a proximal blood vessel signal, a distal blood vessel signal, and a normal blood vessel signal can be measured. The term "proximal blood vessel signal" refers to a signal obtained in a situation in which a blood vessel clamp (not shown) is installed on the vein measured, such that the blood flow rate at a location downstream the clamped position is reduced (reducing the signal strength), and the signal sensing device is mounted downstream the clamped position and is spaced from the blood vessel clamp by about 5 mm. The term "distal blood vessel signal" refers to a signal obtained in a situation in which the signal sensing device is mounted downstream the clamped position and is spaced from the blood vessel clamp by about 10 mm. The term "normal blood vessel signal" refers to a signal obtained in a situation in which no blood vessel clamp is used, such that the vein measured by the signal sensing device is in a natural state. By contrast, in a comparison experiment (published by Stanford University) using pyramidal protruding structures, the optimal size is 50 μm at the base (the maximal side) of the pyramidal protruding structure, and the minimal spacing between the edges of the protruding structures is 40 μm. However, the comparison experiment can only measure the change in the blood flow rate of an artery. Vein is the most common site of thrombus formation after surgery. Therefore, the blood signal of the vein needs to be highly monitored. However, the blood flow fluctuation/signal of a vein is smaller than that of an artery and is, thus, difficult to measure. Therefore, the present invention is a breakthrough to the comparison experiment limited to the measurement of an artery, such that the measured signal has a higher reference value. Specifically, the present invention simulates a thrombus situation of a vein by using a blood vessel clamp, and the signal sensing device according to the present invention can still measure the corresponding blood flow signal to reflect the change in the blood flow of the monitored blood vessel, which significantly increases the applications of the blood vessel signal monitoring. Furthermore, it is noted that the experiment according to the present invention is conducted on a vein of a living animal (such as a rabbit). Particularly, although the diameter of the vein of the experimental living body is smaller than that of a human body, the signal sensing device according to the present invention can still obtain readable signals with a stable quality, which further proves excellent performance on the effects of signal transmission and sensing.

According to the above-mentioned structure disposition of the signal sensing device according to the present invention, the overall signal sensing device (particularly the entirety) may be made of biodegradable material, especially the material approved by the Food and Drug Administration (FDA) of the United States. Therefore, the signal sensing device is particularly suitable for installation in a target organism and can degrade in a predetermined period of time without the need of removal by operation, thereby avoiding the risk caused by the second operation. As an example, the predetermined period of time is 3-26 weeks, preferably 13-26 weeks. However, the predetermined period of time may permit a change in the material, thickness, etc. during the actual period required for monitoring. Thus, the predetermined period of time should not be limited to the above example. In a specific application example, the signal sensing device may be embedded in a human body to measure a blood flow rate (corresponding to the to-be-monitored information) of a blood vessel (corresponding to the to-be-sensed target T).

With regard to the biodegradable material, the body 1 and the insulating material 1 may be comprised of at least one of polyhydroxybutyrate (PHB), polyhydroxyvalerate (PHV), and poly-L-lactic acid (PLLA). The signal sensing element 2 may be comprised of a biodegradable metal, preferably magnesium. The signal amplifying portion 3 may be polycaprolactone (PCL).

It is noted that the thickness of the body 1, particularly the thickness $T_H$ of the head portion 1H and the thickness $T_E$ of the extension portion 1E, refers to the overall thickness of the body 1 including the signal sensing element 2 and other optional elements (such as the insulating layer I).

In view of the foregoing, in the signal sensing device according to the present invention, by the provision of the signal transmission section of the signal sensing element having the meander-line antenna and the misalignment arrangement, the signal transmission quality can be enhanced. By the provision of the protruding structures of the signal amplifying portion protruding from the extension portion of the body and aligned with the signal sensing section of the signal sensing element also located on the extension portion of the body, the strength of the sensing signal (associated with the to-be-monitored information) received by the signal sensing section can be enhanced. Furthermore, by the size disposition of the body, the signal sensing element, and the signal amplifying portion, the signal sensing device is suitable for sensing signals of a specific internal organ or tissue of an organism (particularly a human body). Furthermore, by the provision of the cylindrical protruding structures having a diameter of about 250-400 μm and a height of about 40-75 μm, the strength of the sensing signal can be further enhanced. Furthermore, the overall signal sensing device according to the present invention may be made of a biodegradable material, and by the disposition of the overall size, the signal sensing device is suitable for installation in the human body to sense the interested signal and can degrade completely in a predetermined period of time without the need of removal by operation, thereby avoiding the risk caused by the second operation.

Although the present invention has been described with respect to the above preferred embodiments, these embodiments are not intended to restrict the present invention. Various changes and modifications on the above embodiments made by any person skilled in the art without departing from the spirit and scope of the present invention are still within the technical category protected by the present invention. Accordingly, the scope of the present invention shall include the literal meaning set forth in the appended claims and all changes which come within the range of equivalency of the claims.

What is claimed is:

1. A signal sensing device comprising: a body; and two signal sensing elements disposed in the body, wherein an insulating layer is sandwiched between the two signal sensing elements, wherein each of the two signal sensing elements includes a signal transmission section and a signal sensing section in electrical connection with the signal transmission section, wherein the signal transmission sections are planar antennas parallel to each other and each having an antenna shape of meander-line type, wherein the antenna shape of each transmission section has a vertical projection on a plane parallel to each signal transmission section, and wherein the vertical projections of the antenna shapes do not overlap completely, wherein when a portion of the body forms a surrounding portion which surrounds a to-be-sensed target, a portion or an entirety of each signal sensing section is located on the surrounding portion.

2. The signal sensing device as claimed in claim 1, wherein each antenna shape has a winding section line width of 0.05-0.55 mm, a winding section spacing of 1-4 mm, a winding section overall width of 5-20 mm, a winding section overall length of 5-20 mm, and a thickness of 0.005-0.1 mm.

3. The signal sensing device as claimed in claim 2, wherein the winding section line width is 0.15-0.2 mm, the winding section spacing is 2-3 mm, the winding section overall width is 14-16 mm, the winding section overall length is 14-16 mm, and the thickness is 0.01-0.015 mm.

4. The signal sensing device as claimed in claim 1, wherein the vertical projections of the antenna shapes have a misalignment spacing of 0.05-2 mm.

5. The signal sensing device as claimed in claim 2, wherein the vertical projections of the antenna shapes have a misalignment spacing of 0.1-1.5 mm.

6. The signal sensing device as claimed in claim 3, wherein the vertical projections of the antenna shapes have a misalignment spacing of 0.5-1.5 mm.

7. The signal sensing device as claimed in claim 1, wherein the vertical projections of the antenna shapes each have an X-direction misalignment spacing in an X direction and a Y-direction misalignment spacing in a Y direction perpendicular to the X direction, and wherein each of the X-direction misalignment spacing and the Y-direction misalignment spacing is 0.05-2 mm.

8. The signal sensing device as claimed in claim 1, wherein the body includes a head portion and an extension portion connected to the head portion, wherein the extension portion extends outward from an end of the head portion and has a length to surround the to-be-sensed target by an entirety or a portion of the extension portion.

9. The signal sensing device as claimed in claim 8, wherein each signal transmission section is disposed on the head portion of the body, and wherein each signal sensing section is disposed on the extension portion of the body.

10. The signal sensing device as claimed in claim 9, wherein the head portion of the body has a length and a width both of which are 5-35 mm, wherein the extension portion has a width of 2-15 mm, and wherein each of the head portion and the extension portion has a thickness of 0.05-0.350 mm.

11. The signal sensing device as claimed in claim 1, further comprising a signal amplifying portion having a plurality of protruding structures protruding outward from the body, wherein each of the plurality of protruding structures is cylindrical and has a diameter of 250-400 μm and a height of 40-75 μm, and wherein when the surrounding portion is formed by a portion of the body, the signal amplifying portion is partially or entirely in contact with the to-be-sensed target.

12. The signal sensing device as claimed in claim 11, wherein the diameter of each of the plurality of protruding structures is 300-350 μm, and wherein the height of each of the plurality of protruding structures is 50 μm.

13. The signal sensing device as claimed in claim 1, wherein the signal sensing device is made of one or more bio-degradable materials.

* * * * *